US011230665B2

(12) United States Patent
Soer et al.

(10) Patent No.: US 11,230,665 B2
(45) Date of Patent: *Jan. 25, 2022

(54) LIGHTING SYSTEM HAVING REDUCED MELANOPIC SPECTRAL CONTENT

(71) Applicant: LUMILEDS LLC, San Jose, CA (US)

(72) Inventors: Wouter A. Soer, San Jose, CA (US); Oleg B. Shchekin, San Jose, CA (US); Hans-Helmut Bechtel, San Jose, CA (US)

(73) Assignee: LUMILEDS LLC, San Jose, CA (US)

( * ) Notice: Subject to any disclaimer, the term of this patent is extended or adjusted under 35 U.S.C. 154(b) by 2 days.

This patent is subject to a terminal disclaimer.

(21) Appl. No.: 16/332,319

(22) PCT Filed: Sep. 12, 2017

(86) PCT No.: PCT/US2017/051170

§ 371 (c)(1),
(2) Date: Mar. 11, 2019

(87) PCT Pub. No.: WO2018/049397

PCT Pub. Date: Mar. 15, 2018

(65) Prior Publication Data

US 2019/0219234 A1 Jul. 18, 2019

Related U.S. Application Data

(60) Provisional application No. 62/393,306, filed on Sep. 12, 2016.

(51) Int. Cl.
*C09K 11/77* (2006.01)
*H05B 45/20* (2020.01)
(Continued)

(52) U.S. Cl.
CPC ......... *C09K 11/7734* (2013.01); *A61M 21/00* (2013.01); *F21K 9/64* (2016.08);
(Continued)

(58) Field of Classification Search
CPC ..... F21K 9/64; C09K 11/7734; H01L 33/502; H01L 27/156; H01L 33/505; H05B 45/20;
(Continued)

(56) References Cited

U.S. PATENT DOCUMENTS 8,251,538 B2 8/2012 Samber et al.
9,024,536 B2 5/2015 Maxik et al.
(Continued)

FOREIGN PATENT DOCUMENTS

JP 2007524119 A 8/2007
JP 2015097196 A 5/2015
(Continued)

OTHER PUBLICATIONS

International Search Report corresponding to PCT/US2017/051170, dated Nov. 7, 2017, 1 page.
(Continued)

*Primary Examiner* — Bilkis Jahan
*Assistant Examiner* — Victor V Barzykin

(57) ABSTRACT

A disclosed light-emitting device may provide white light with a cyan gap coinciding with a melanopic sensitivity range and thus having reduced melanopic content. The disclosed light-emitting device may include a light source providing violet or blue light with a peak wavelength under 450 nanometers (nm). The disclosed light-emitting device may include at least one down-converter coupled to and located downstream of the light source and configured with a long-wavelength onset to convert the spectrum of the violet or blue light to generate white light with a spectral power content in a 447-531 nm wavelength range that is less
(Continued)

than or equal to 10% of a total spectral power content in a 380-780 nm wavelength range. The disclosed light-emitting device may be incorporated in a light engine system that further includes a control system that controls a drive current to the light-emitting device.

20 Claims, 3 Drawing Sheets

(51) Int. Cl.

| | |
|---|---|
| ***F21K 9/64*** | (2016.01) |
| ***A61M 21/00*** | (2006.01) |
| ***F21V 23/00*** | (2015.01) |
| ***H01L 27/15*** | (2006.01) |
| ***H01L 33/50*** | (2010.01) |
| *F21Y 115/10* | (2016.01) |

(52) U.S. Cl.
CPC .......... *F21V 23/003* (2013.01); *H01L 27/156* (2013.01); *H01L 33/502* (2013.01); *H01L 33/505* (2013.01); *H05B 45/20* (2020.01); *A61M 2021/0044* (2013.01); *F21Y 2115/10* (2016.08); *Y02B 20/00* (2013.01)

(58) Field of Classification Search
CPC ... F21V 23/003; F21Y 2115/10; Y02B 20/181
See application file for complete search history.

(56) References Cited

U.S. PATENT DOCUMENTS

| | | | | |
|---|---|---|---|---|
| 9,410,664 | B2 | 8/2016 | Krames et al. | |
| 2009/0212698 | A1* | 8/2009 | Bailey | F21K 9/232 313/512 |
| 2009/0281604 | A1 | 11/2009 | De Boer et al. | |
| 2011/0137757 | A1 | 6/2011 | Paolini et al. | |
| 2012/0019138 | A1 | 1/2012 | Maxik et al. | |
| 2014/0301062 | A1 | 10/2014 | David et al. | |
| 2015/0062892 | A1* | 3/2015 | Krames | F21K 9/64 362/231 |
| 2015/0214444 | A1* | 7/2015 | Watanabe | H01L 33/502 257/98 |
| 2016/0116124 | A1 | 4/2016 | Podowitz et al. | |
| 2016/0377262 | A1* | 12/2016 | Krames | F21V 19/006 315/297 |
| 2017/0368210 | A1* | 12/2017 | David | H01L 33/00 |
| 2018/0128431 | A1 | 5/2018 | Heilman et al. | |

FOREIGN PATENT DOCUMENTS

| | | | |
|---|---|---|---|
| JP | 2015163689 | A | 9/2015 |
| TW | 201307756 | A | 2/2013 |
| WO | 2015/060701 | A1 | 4/2015 |

OTHER PUBLICATIONS

From the EPO as the ISA, International Search Report and Written Opinion, PCT/US2017/051170, dated Nov. 7, 2017, 10 pages.

* cited by examiner

| | LED 201 | LED 202 | LED 203 | LED 204 |
|---|---|---|---|---|
| CCT (K) | 4001 | 3170 | 3008 | 3064 |
| Duv | 0.0047 | 0.0014 | 0.0009 | 0.0007 |
| LER (lm/W) | 342 | 397 | 434 | 382 |
| CRI Ra | 76 | 41 | 40 | 66 |
| TM-30 Rf | 76 | 35 | 35 | 51 |
| TM-30 Rg | 91 | 79 | 78 | 101 |
| TM-30 color vector graphic | COLOR VECTOR GRAPHIC<br>— Reference Illuminant<br>- - - Test Source | COLOR VECTOR GRAPHIC<br>— Reference Illuminant<br>- - - Test Source | COLOR VECTOR GRAPHIC<br>— Reference Illuminant<br>- - - Test Source | COLOR VECTOR GRAPHIC<br>— Reference Illuminant<br>- - - Test Source |
| m/p ratio | 0.63 | 0.28 | 0.26 | 0.30 |
| Radiometric melanopic content | 26% | 5% | 5% | 5% |

FIG. 3

LIGHTING SYSTEM HAVING REDUCED MELANOPIC SPECTRAL CONTENT

CROSS REFERENCE TO RELATED APPLICATION

This application is a U.S. National Phase application under 35 U.S.C. 371 of International Patent Application PCT/US2017/051170 filed Sep. 12, 2017, which claims the benefit of U.S. provisional application No. 62/393,306 filed Sep. 12, 2016, both of which are incorporated herein by reference in their entirety.

FIELD OF INVENTION

The disclosures herein generally relate to a light-emitting device with an improved non-visual response.

BACKGROUND

A light-emitting diode (LED) is a semiconductor light emitter used as a light source in a variety of applications, such as display lights, warning lights, indicator lights, or other applications where white or colored light is desired. The color of light produced by an LED is determined, at least in part, by the type of semiconducting material used in its manufacture. For LEDs used in general illumination applications (e.g., general or ambient lighting), the emission spectrum (i.e., intensity of light versus its wavelength) may be the result of a compromise between a preferred color point and color rendition (the effect of a light source on the color appearance of objects and an aspect of color quality) on the one hand, and (luminous) efficacy on the other hand, due to the limitations of practical emitter and converter materials.

In an example, existing LED designs for outdoor and industrial applications often prioritize efficacy over color quality because such applications typically have long operating hours providing potential to exploit significant energy savings, and often do not need high color fidelity. These characteristics, associated with outdoor and industrial applications, have led to a prevalence of LEDs with cool-white and neutral-white correlated color temperatures (CCT) (e.g., CCT values of 4000 Kelvin (K) and above) with moderate color rendering index (CRI) (CRI is a scale from 0 to 100 percent indicating how accurate a given light source is at rendering color when compared to a "reference" light source). An example of a cool-white LED with moderate CRI is a 4000K/70 LED with CCT equal to 4000K and a CRI value of 70. The emission spectra associated with such existing LEDs as the 4000K/70 LED have significantly more blue spectral content than some of the incumbent technologies that they replace (e.g., high-pressure sodium lighting), which has caused recent concerns about their impact on human physiology, and in particular circadian rhythms.

SUMMARY

A disclosed light-emitting device may provide white light with a cyan gap coinciding with a melanopic sensitivity range and thus having reduced melanopic content. The disclosed light-emitting device may include a light source providing violet or blue light with a peak wavelength under 450 nanometers (nm) (e.g., 410-420 nm, 420-430 nm, 430-440 nm or 440-450 nm). The disclosed light-emitting device may include at least one down-converter coupled to and located downstream of the light source and configured with a long-wavelength onset to convert the spectrum of the violet or blue light to generate white light with a spectral power content in a 447-531 nm wavelength range that is less than or equal to 10% of a total spectral power content in a 380-780 nm wavelength range. The disclosed light-emitting device may provide white light with a correlated color temperature (CCT) of at least 2700 Kelvin (K). The at least one down-converter may be a nitride-based phosphor system with peak emission in an amber wavelength range. Examples materials for the nitride-based phosphor system include $(Ba,Sr)_2Si_5N_8$:Eu (BSSN) and/or $(Sr,Ca)SiAlN_3$:Eu (SCASN). The disclosed light-emitting device may be incorporated in a light engine system that further includes a control system that controls a drive current to the light-emitting device.

BRIEF DESCRIPTION OF THE DRAWINGS

FIG. 3 is a table showing spectral metrics for the light-emitting devices with spectra shown in FIG. 2.

DETAILED DESCRIPTION OF THE EMBODIMENTS

Figure 1:
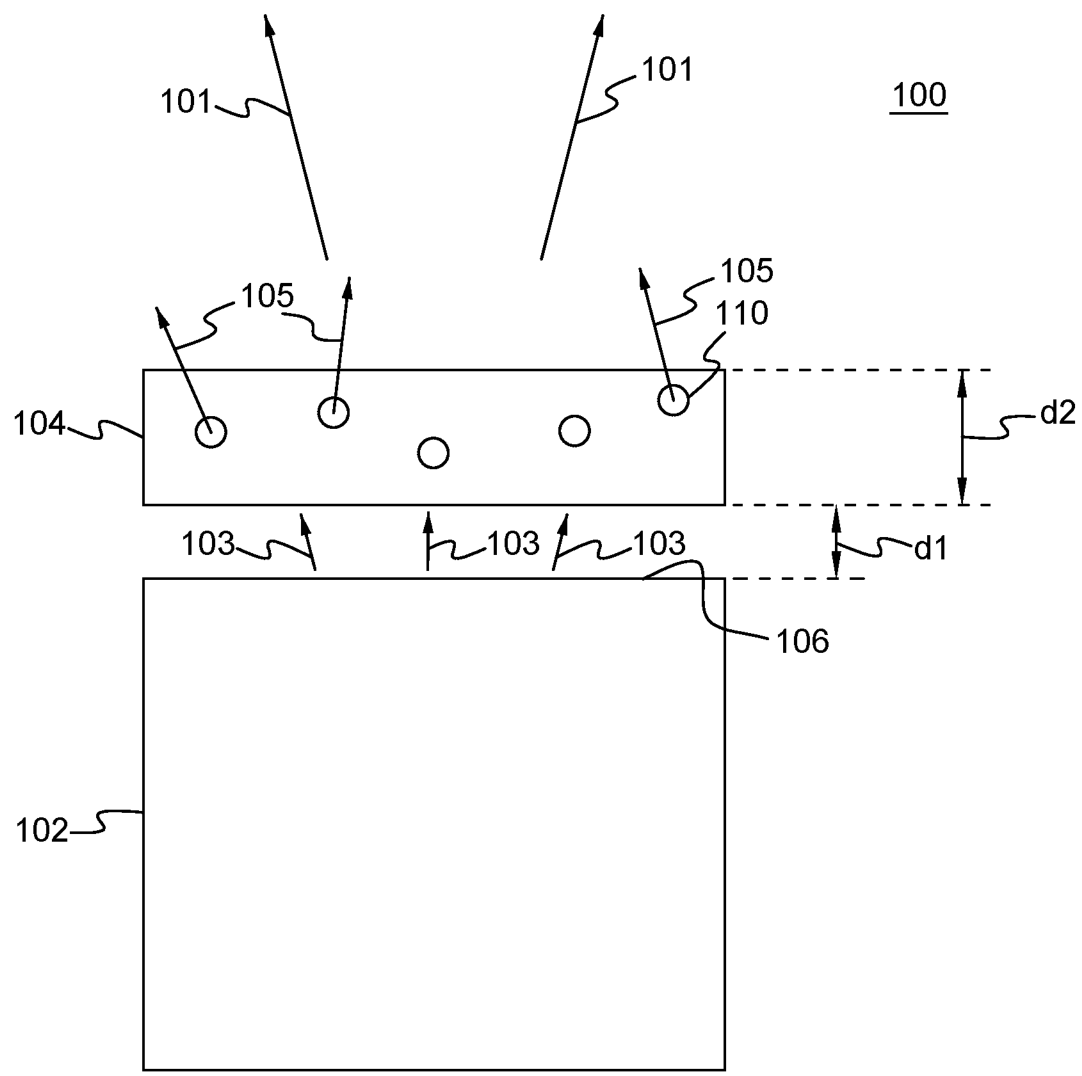
FIG. 1 is a schematic diagram of an example light-emitting device, in accordance with the disclosures herein.

The human circadian rhythm is a twenty-four hour cycle in the human physiological process and includes any biological process that displays an endogenous and entrainable oscillation. Entrainment is the interaction between circadian rhythms and the environment, such as the entrainment of circadian rhythms to the daily light-dark cycle determined by the earth's rotation.

Light-induced circadian entrainment and other non-visual responses to light are influenced by a distinct photoreceptor in the eye, the intrinsically photosensitive retinal ganglion cells (ipRGCs), in addition to conventional rods and cones. Together, these responses can produce a day-like physiological state. For example, light constricts the pupil, suppresses pineal melatonin production, increases heart rate and core body temperature, stimulates cortisol production, and acts as a neurophysiological stimulant.

Empirical evidence has shown that these non-visual responses generally have a peak spectral sensitivity in the short-wavelength end of the visible spectrum. This correlates with the action spectrum for melanopsin, which is the photopigment (i.e., a pigment whose chemical state depends on its degree of illumination) in the eye expressed by the ipRGCs, and which peaks at a wavelength of 490 nm. The melanopic sensitivity range is 447-531 nm full width at half maximum (FWHM) (i.e., the width of the spectral density curve between points on the curve at which the spectral density reaches half its maximum value). However, the firing pattern of the ipRGCs is based not only on melanopsin phototransduction but also on inputs from rods and cones, due to their neurophysiological connections. Therefore, the spectral sensitivity of non-visual responses is generally more complex as it is affected by the total spectrum and illuminance (i.e., the amount of luminous flux per unit area) and may be different between specific physiological responses. Tools are available to calculate, for a given spectrum, the spectrally weighted irradiance (the flux of radiant energy per unit area) of the five human photopigments, which are well established. These tools can then be used as a starting point to study and quantify the ability of spectra to evoke non-visual responses.

In many lighting applications, including general purpose, outdoor and industrial applications, it is desirable to minimize non-visual responses while providing adequate visual illuminance with high energy efficiency, which may be accomplished by minimizing the spectral content in the melanopic sensitivity range. Existing neutral-white phosphor-converted LEDs (pc-LEDs) have significant spectral content in the melanopic sensitivity range (447-531 nm FWHM), which may be a dominant factor for non-visual responses. For example, the spectral power content in the melanopic sensitivity range for a typical 4000K/70 LED is 26%.

With conventional white light pc-LEDs, reducing the spectral content in the melanopic sensitivity range while maintaining a color point on the blackbody locus (i.e., a color on the path that the color of an incandescent black body would take in a particular chromaticity space as the blackbody temperature changes) may involve moving to a deep-warm-white color. An example of a deep-warm-white color LED is a 2200K/80 LED, which has 11% spectral power content in the melanopic range. However, a 2200K/80 LED is generally not desirable because of an undesirable color point (most applications specify light between 27000K and 4000K) and the much lower efficacy. Warm-white light sources need significant red to deep red spectral content to maintain good color rendering. At the associated wavelengths (e.g., 620-750 nm), the sensitivity of the human eye is relatively low and therefore the luminous efficacy (in units of lumens per Watt, lm/W) is low and inefficiencies are increased from emitting a spectrum where a large fraction of the emitted wavelengths are beyond the sensitivity of the human eye.

Accordingly, to address the concerns raised above, a pc-LED is disclosed with an emission spectrum that minimizes spectral content in the melanopic sensitivity range while still achieving a white color point with a CCT of 2700K or higher, allowing for high (luminous) efficacy. The disclosed pc-LED may be realized using a short-wavelength pump LED (e.g., a blue or violet LED) and a converter, coupled to and located above the short-wavelength pump LED, having a long-wavelength onset of the emission spectrum, thereby creating a cyan gap in the emitted spectrum coinciding with the melanopic range. An example of a converter is a phosphor layer or coating on or above the short-wavelength pump LED, such that the light (photons) generated by the LED travel through the phosphor layer. The disclosed pc-LED achieves a spectral power content in the melanopic range of approximately 5% while achieving a luminous efficacy of radiation (LER) that is improved by approximately 15% over a state-of-the-art 4000K/70 LED. The disclosed LED is described in more detail below.

Although the example embodiments may be described herein with respect to an LED light source and a phosphor-based converter, any other light source (e.g., a laser diode) and/or converter (quantum dot converter) may be used similarly.

In an example embodiment, the disclosed light-emitting device is a violet or blue pc-LED (or laser diode) with a pump wavelength of 450 nm or less (e.g., 410-420 nm, 420-430 nm, 430-440 nm or 440-450 nm) and a total emission spectrum, once converted, that has a substantially white color point with a CCT of 2700K or higher, and a spectral power content in the 447-531 nm wavelength range of 10% or less of the total power between 380 nm and 780 nm.

In an example embodiment, the disclosed light-emitting device may be an LED with a nitride-based phosphor system with peak emission in the amber wavelength range, which is approximately 570-600 nm. Examples of materials for the phosphor system may include, but is not limited to, $(Ba,Sr)_2Si_5N_8$:Eu ("BSSN"), $(Sr,Ca)SiAlN_3$:Eu ("SCASN"), a mixture of both BSSN and SCASN, and/or any phosphor with emission in the desired amber wavelength range. In an example, the disclosed LED may be a high-power flip-chip die and the phosphor may be integrated as a ceramic plate attached to the die. However, other pc-LED device architectures may similarly be employed.

In another example embodiment, the disclosed light-emitting device may be incorporated in a light engine that also includes one or more light-emitters each with a cyan enhanced spectrum, and a control system that controls the drive current of the cyan depleted and cyan enhanced emitters. The control system may then be configured to suppress or evoke non-visual responses depending on application needs.

FIG. 1 is a schematic diagram of an example light-emitting device 100, in accordance with the disclosures herein. The light-emitting device 100 may be configured to provide white light 101. The light-emitting device 100 may include a light source 102 configured to provide light source light 103. For example, the light source 102 may provide violet to blue light source light 103, with a wavelength in the range of 400-460 nm (e.g., 410-450 nm). In an example, the light source 102 may be implemented as a pump LED, such as violet pump LED or a blue pump LED. For example, the light source 102 may be high-power flip-chip die.

The light-emitting device 100 may include a luminescent material element 104. For example, the luminescent material element 104 may include one or more converters, such as one or more narrow-band converters (e.g., quantum dot converters). For example, the luminescent material element 104 may comprise down-converter(s) or down-converting material that converts high-energy photons provided by the light source 102 into lower-energy photons to constitute the rest of the spectrum. In an example, the luminescent material element 104 may be a nitride-based phosphor system and may consist of a phosphor material, such as any of the examples described herein. In an example, the luminescent material element 104 may be ceramic plate attached to the light source 102. The luminescent material element 104 may be located downstream (in the direction of light emittance) of the light source 102 and in particular with respect to the light emitting surface 106 of the light source 102. The material used in the luminescent material element 104 may be configured to absorb at least part of the light source light 103 (e.g., violet light or blue light) and may convert the light source light 103 into luminescent material light 105. The luminescent material element 104 may be transmissive (i.e., allowing light to pass through) for at least part of the light source light 103. The luminescent material element 104 may have waveguiding properties. Thus, the white light 101 emitted from the light-emitting device 100 may include at least some portion of the light source light 103 and at least some portion of the luminescent material light 105.

In an example, the luminescent material element 104 may include a luminescent material 110, which provides the luminescent material light 105. In this example, the luminescent material 110 is indicated as particles or regions within the luminescent material element 104. However, the luminescent material 110 may be homogeneously distributed over the luminescent material element 104. In an example, the luminescent material 110 may be consist of phosphor to provide a yellow light, and/or provide a broader combined emission spectrum extending into red light.

The distance between the luminescent material element 104 and the light emitting surface 106 of the light source 102 is indicated by d1. For example, the distance d1 may be practically 0 mm (e.g., the luminescent material element 104 may be in physical contact with the light emitting surface 106 of the light source 102, or separated by a transparent substrate or glue bond of only a few μm in thickness) or may be larger than 0 mm (e.g., 10 mm). In an example, the thickness d2 of the luminescent material element 104 may be in the range of a 5 μm to 10 mm. The thickness d2 may depend upon the type of application (e.g., thinner layer thicknesses for non-remote or vicinity applications, and larger layer thicknesses d2 for remote applications).

Figure 2:
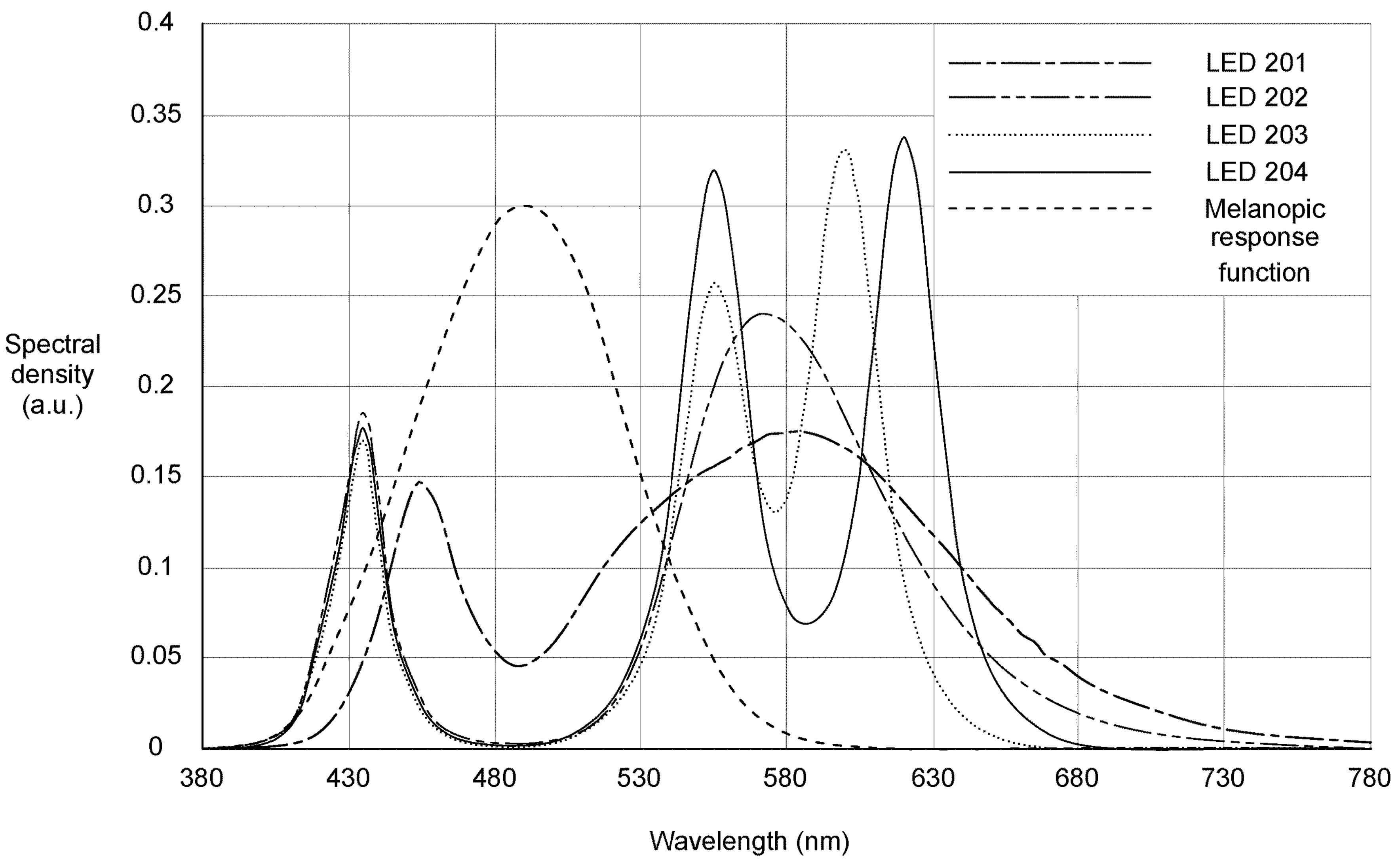
FIG. 2 is a diagram of the spectra or spectral densities of several light-emitting devices configured to emit white light with reduced spectral content in the melanopic sensitivity range, as shown compared to the melanopic response function.

FIG. 2 is a diagram of the spectra or spectral densities (shown normalized in arbitrary units (a.u.)) of several light-emitting devices configured to emit white light with reduced spectral content in the melanopic sensitivity range, as shown compared to the melanopic response function (shown by a dashed line). Metrics for the spectra represented in FIG. 2 are given in FIG. 3. The luminous efficacy of radiation (LER), measured in lumens per Watt (lm/W), is the ratio of luminous flux to power and provides a measure of how well a light source produces visible light. The CRI indicates, on a scale of 0-100, how accurately a given light source renders color when compared to a reference light source (CRI Ra refers to the average of the first eight indices defined in CRI).

The light-emitting devices represented in FIG. 2 are: LED 201 (shown by a long dash/short dash line), which may be a state-of-the-art 4000K/70 LED; LED 202 (shown by a long dash/double short dash line), which may be an example 3000K pc-LED, as implemented in accordance with the disclosures herein; LED 203 (shown by a dotted line), which may be another example 3000K LED with further improved LER, as implemented in accordance with the disclosures herein; and LED 204 (shown by a solid line), which may be another example 3000K LED with improved CRI, as implemented in accordance with the disclosures herein.

The spectral densities shown in FIG. 2 exhibit reduced melanopic illuminance (in the range of approximately 447-531 nm FWHM) at a given photopic illuminance. As illustrated by the spectra shown in FIG. 2 and the corresponding data in FIG. 3, the example LEDs 202, 203 and 204, implemented in accordance with the disclosures herein, have significantly higher LER (397 lm/W, 434 lm/W, and 382 lm/W, respectively) than the LER of the state-of-the-art 4000K/70 LED 201 (342 lm/W). Moreover, the ceramic plate technology (e.g., phosphor based) that may be used as a converter in the light-emitting device can reduce scattering compared to phosphor integration technologies using phosphor powder, which may further increase the overall luminous efficacy.

In an example, the LED 203 and/or LED 204 may contain one or more narrow-band converters, for example quantum dot converters, to realize the respective desired spectrum shown in FIG. 2. By design, creating a cyan gap, as shown in the spectra in FIG. 2, may desaturate cyan colors while oversaturating the violet-blue and green-yellow colors adjacent to the cyan gap. By tuning the remainder of the emission spectrum, the impact on such saturation and desaturation on color rendering can be minimized and a CRI above 60 can be achieved while still maintaining minimal cyan content. The excellent color rendering at long wavelengths compensates for poorer color rendering of short wavelengths to achieve the acceptable overall CRI.

FIG. 3 shows key spectral metrics for chromaticity, LER, color rendering (CRI) and melanopic spectral content for each of the LED light-emitter designs with spectra shown in FIG. 2. The example LEDs 201-204 have small "Duv" values, which is the distance to the blackbody locus in CIE1976 color space, and thus indicate a white color for the example LEDs 201-204. As explained above, the example LEDs 202, 203 and 204, implemented in accordance with the disclosures herein, have higher LER, and thus an improved luminous efficacy, than the LER of the state-of-the-art 4000K/70 LED 201. TM-30 is a color rendering metric that consists of fidelity (TM-30 Rf), gamut (TM-30 Rg), and TM-30 color vector graphic showing saturation of individual colors. The melanopic spectral content may be represented by the fraction of radiometric power within the melanopic FWHM of 447-531 nm, or by the ratio of melanopic lux and photopic lux (m/p ratio). The latter more accurately reflects the weighting by the melanopic sensitivity curve.

The disclosures described herein include example embodiments, such that a person skilled in the art could modify, alter, omit or replace the described elements with equivalent elements.

What is claimed is:

1. A light-emitting device configured to provide white light with a cyan gap coinciding with a melanopic sensitivity range, the light-emitting device comprising:

a light source configured to emit violet or blue light with an emission spectrum having peak wavelength under 450 nm; and at least one wavelength converter coupled to and located downstream of the light source and configured to absorb at least a portion of violet or blue light emitted by the light source and in response emit light with an emission spectrum at wavelengths longer than those in the light source emission spectrum;

an unabsorbed portion of the violet or blue light emitted by the light source and transmitted through the wavelength converter combined with the emission from the wavelength converter providing a white light emission spectrum from the light emitting device, the white light emission spectrum having a correlated color temperature greater than or equal to 2700 K, comprising a spectral gap in a 447 nm-531 nm wavelength range defined by a long wavelength side of the light source emission spectrum and a short wavelength side of the wavelength converter emission spectrum, and having a spectral power content in the 447-531 nm wavelength range that is less than or equal to 10% of a total spectral power content in a 380 nm-780 nm wavelength range, and a spectral power density value at 447 nm that is greater than a spectral power density value at 500 nm, and the white light emission spectrum having a luminous efficacy of radiation greater than 380 lumens per Watt.

2. The light emitting device of claim 1, wherein the white light emission spectrum has a spectral power content in the 447-531 nm wavelength range that is less than or equal to 5% of a total spectral power content in a 380 nm-780 nm wavelength range.

3. The light emitting device of claim 1, wherein the white light emission has a spectral power content between 447 nm and 470 nm greater than a spectral power content of the white light emission between 470 nm and 510 nm.

4. The light emitting device of claim 1, wherein the white light emission has a spectral power content between 380 nm and 447 nm that is less than a spectral power content between 531 nm and 630 nm.

5. The light emitting device of claim 1, wherein the light source is configured to emit light with an emission spectrum having peak wavelength less than or equal to 440 nm.

6. The light emitting device of claim 1, wherein:
the white light emission has a minimum spectral power density value at a wavelength between 480 nm and 490 nm.

7. The light emitting device of claim 1, wherein the wavelength converter is configured to absorb at least a portion of violet or blue light emitted by the light source and in response emit light with an emission spectrum having a peak in the amber wavelength range and extending into the red wavelength range.

8. The light emitting device of claim 7, wherein the wavelength converter comprises a nitride-based phosphor.

9. The light emitting device of claim 8, wherein the a nitride-based phosphor comprises one or more of $(Ba,Sr)_2Si_5N_8:Eu$, $(Sr,Ca)SiAlN_3:Eu$, or $(Ba,Sr)_2Si_5N_8:Eu$ and $(Sr,Ca)SiAlN_3:Eu$.

10. The light emitting device of claim 7, wherein a short wavelength side of the peak in the amber wavelength range forms a long wavelength side of the spectral gap.

11. The light emitting device of claim 1, wherein the wavelength converter comprises quantum dots configured to absorb at least a portion of the violet or blue light emitted by the light source and in response emit light with an emission spectrum at wavelengths longer than those in the light source emission spectrum.

12. The light emitting device of claim 1, wherein the light source is a light emitting diode or laser diode.

13. The light emitting device of claim 1, wherein the wavelength converter is in contact with a light emitting surface of the light source.

14. The light emitting device of claim 13, wherein the wavelength converter comprises a ceramic plate attached to the light emitting surface of the light source.

15. The light emitting device of claim 1, wherein the wavelength converter is located at a non-zero distance from a light emitting surface of the light source.

16. A light engine configured to provide white light with tunable spectral content in a range coinciding with a melanopic sensitivity range, the light engine comprising:
a plurality of the light-emitting devices of claim 1; and
a control system configured to control drive current to the plurality of light-emitting devices.

17. The light emitting device of claim 16, wherein the white light emission spectrum of the light-emitting devices has a spectral power content in the 447-531 nm wavelength range that is less than or equal to 5% of a total spectral power content in a 380 nm-780 nm wavelength range.

18. The light emitting device of claim 1, wherein the violet or blue light has an emission spectrum having peak wavelength greater than 430 nm.

19. The light emitting device of claim 1, wherein the white light emission spectrum has a first long wavelength peak between 530 nm and 580 nm, a second long wavelength peak between 580 nm and 630 nm, and essentially zero spectral content above wavelength of 690 nm.

20. A light-emitting device comprising:
a light source configured to emit violet or blue light with an emission spectrum having peak wavelength under 450 nm; and
at least one wavelength converter coupled to and located downstream of the light source and configured to absorb at least a portion of violet or blue light emitted by the light source and in response emit light with an emission spectrum at wavelengths longer than those in the light source emission spectrum;
the light source and the at least one wavelength converter configured to emit a white light emission spectrum comprising an unabsorbed portion of the violet or blue light emitted by the light source and transmitted through the wavelength converter combined with the emission from the wavelength converter, the white light emission spectrum having a correlated color temperature greater than or equal to 2700 K, a luminous efficacy of radiation greater than 380 lumens per watt, and comprising a spectrum in a 380 nm 780 nm range having a spectral gap in the 447 nm 531 nm range, with a spectral power content in the spectral gap that is less than or equal to 10% of a total spectral power content over the spectrum in the 380 nm-780 nm range.

* * * * *

UNITED STATES PATENT AND TRADEMARK OFFICE

CERTIFICATE OF CORRECTION

PATENT NO. : 11,230,665 B2
APPLICATION NO. : 16/332319
DATED : January 25, 2022
INVENTOR(S) : Wouter A. Soer, Oleg B. Shchekin and Hans-Helmut Bechtel It is certified that error appears in the above-identified patent and that said Letters Patent is hereby corrected as shown below:

On the Title Page

Item (72) Line 1 should read: -- Wouter A. Soer, Utrecht (NL) --

Item (72) Line 3 should read: -- Hans-Helmut Bechtel, Roetgen (DE) --

In the Claims

Column 8, Line 38 should read: -- 380 nm – 780 nm --

Column 8, Line 39 should read: -- 447 nm – 531 nm --

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*